(12) United States Patent
Johnson et al.

(10) Patent No.: US 9,798,151 B2
(45) Date of Patent: Oct. 24, 2017

(54) AUTOSTEREOSCOPIC DISPLAY DEVICE

(75) Inventors: Mark Thomas Johnson, Arendonk (BE); Marcellinus Petrus Carolus Michael Krijn, Eindhoven (NL); Bart Kroon, Eindhoven (NL); Philip Steven Newton, Eindhoven (NL); Adrianus Sempel, Waalre (NL); Siebe Tjerk De Zwart, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 418 days.

(21) Appl. No.: 14/126,101

(22) PCT Filed: Jun. 7, 2012

(86) PCT No.: PCT/IB2012/052875
§ 371 (c)(1),
(2), (4) Date: Dec. 13, 2013

(87) PCT Pub. No.: WO2012/176089
PCT Pub. Date: Dec. 27, 2012

(65) Prior Publication Data
US 2014/0111855 A1    Apr. 24, 2014

(30) Foreign Application Priority Data
Jun. 22, 2011   (EP) ..................... 11170972

(51) Int. Cl.
*G02B 27/22* (2006.01)
*H04N 13/04* (2006.01)
(Continued)

(52) U.S. Cl.
CPC ...... *G02B 27/2214* (2013.01); *H01L 51/5275* (2013.01); *H04N 13/0404* (2013.01);
(Continued)

(58) Field of Classification Search
CPC .................. G02B 27/22; G02B 27/2207; G02B 27/2214; G02B 27/225; G02B 6/0001; H04N 13/0404; G09G 2320/0209
(Continued)

(56) References Cited

U.S. PATENT DOCUMENTS 6,504,981 B1   1/2003  Morley
7,450,304 B2   11/2008 Sakai et al.
(Continued)

FOREIGN PATENT DOCUMENTS

EP    1385219 A2    1/2004

OTHER PUBLICATIONS

Mehta, D.S. et al "Light Out-Coupling Strategies in Organic Light Emitting Devices", Proc. of ASID, 2006, New Delhi.

*Primary Examiner* — Darryl J Collins
*Assistant Examiner* — Journey Sumlar

(57) ABSTRACT

An autostereoscopic display device comprises a display arrangement such as an emissive display arrangement or an reflective display arrangement, with an array of spaced pixels. A light guiding arrangement has an array of light guide columns, with one column over each display pixel or over a group (such as a column) of pixels. The light guide columns comprise aside wall which tapers outwardly to define a funnel shape with the pixel at the smaller base of the funnel. The funnel provides collimation to reduce cross talk in the display, which is particularly problematic for 3D autostereoscopic displays.

15 Claims, 7 Drawing Sheets

(51) Int. Cl.
*H01L 51/52* (2006.01)
*G02F 1/1335* (2006.01)
*H01L 27/32* (2006.01)

(52) U.S. Cl.
CPC .... *G02F 1/133524* (2013.01); *H01L 27/3241* (2013.01); *H04N 2213/001* (2013.01)

(58) Field of Classification Search
USPC .................................... 359/462, 463, 457
See application file for complete search history.

(56) References Cited

U.S. PATENT DOCUMENTS

| | | | |
|---|---|---|---|
| 8,378,361 B2 | 2/2013 | Takeuchi | |
| 2004/0042198 A1* | 3/2004 | Cok | 362/84 |
| 2006/0203336 A1 | 9/2006 | Van Berkel | |
| 2006/0245060 A1 | 11/2006 | Goto | |
| 2008/0030882 A1 | 2/2008 | Ichikawa | |
| 2008/0144174 A1 | 6/2008 | Lucente | |
| 2010/0201256 A1 | 8/2010 | Xue | |
| 2011/0193107 A1 | 8/2011 | Takeuchi | |
| 2011/0234605 A1* | 9/2011 | Smith | G02B 27/2214 345/522 |
| 2012/0099193 A1 | 4/2012 | Yang et al. | |
| 2012/0262943 A1 | 10/2012 | Urabe | |
| 2014/0320733 A1* | 10/2014 | Ikemoto | H04N 5/23212 348/348 |

* cited by examiner

AUTOSTEREOSCOPIC DISPLAY DEVICE

CROSS-REFERENCE TO PRIOR APPLICATIONS

This application is the U.S. National Phase application under 35 U.S.C. §371 of International Application No. PCT/IB2012/052875, filed on Jun. 7, 2012, which claims the benefit of European Patent Application No. 11170972.1, filed on Jun. 22, 2011. These applications are hereby incorporated by reference herein.

FIELD OF THE INVENTION

This invention relates to an autostereoscopic display device of the type that comprises a display panel having an array of display pixels for producing a display and an imaging arrangement for directing different views to different spatial positions.

BACKGROUND OF THE INVENTION

A first example of an imaging arrangement for use in this type of display is a barrier, for example with slits that are sized and positioned in relation to the underlying pixels of the display. In a two-view design, the viewer is able to perceive a 3D image if his/her head is at a fixed position. The barrier is positioned in front of the display panel and is designed so that light from the odd and even pixel columns is directed towards the left and right eye of the viewer, respectively.

A drawback of this type of two-view display design is that the viewer has to be at a fixed position, and can only move approximately 3 cm to the left or right. In a more preferred embodiment there are not two sub-pixel columns beneath each slit, but several. In this way, the viewer is allowed to move to the left and right and perceive a stereo image in his/her eyes all the time.

The barrier arrangement is simple to produce but is not light efficient. A preferred alternative is therefore to use a lens arrangement as the imaging arrangement. For example, an array of elongate lenticular elements can be provided extending parallel to one another and overlying the display pixel array, and the display pixels are observed through these lenticular elements.

The lenticular elements are provided as a sheet of elements, each of which comprises an elongate semi-cylindrical lens element. The lenticular elements extend in the column direction of the display panel, with each lenticular element overlying a respective group of two or more adjacent columns of display pixels.

In an arrangement in which, for example, each lenticule is associated with two columns of display pixels, the display pixels in each column provide a vertical slice of a respective two dimensional sub-image. The lenticular sheet directs these two slices and corresponding slices from the display pixel columns associated with the other lenticules, to the left and right eyes of a user positioned in front of the sheet, so that the user observes a single stereoscopic image. The sheet of lenticular elements thus provides a light output directing function.

In other arrangements, each lenticule is associated with a group of four or more adjacent display pixels in the row direction. Corresponding columns of display pixels in each group are arranged appropriately to provide a vertical slice from a respective two dimensional sub-image. As a user's head is moved from left to right, a series of successive, different, stereoscopic views are perceived creating, for example, a look-around impression.

Known autostereoscopic displays use liquid crystal displays to generate the image.

There is increasing interest in the use of emissive displays, such as electroluminescent displays, for example organic light emitting diode (OLED) displays, as these do not need polarizers, and potentially they should be able to offer increased efficiency since the pixels are turned off when not used to display an image, compared to LCD panels which use a continuously illuminated backlight.

There is also increasing interest in the use of reflective displays, such as electrophoretic displays and electrowetting displays.

This invention is based on the use, within an autostereoscopic display system, of a display arrangement that is emissive or reflective.

Emissive displays such as OLED displays and reflective displays such as electrophoretic displays differ significantly from LCD displays in how the light is emitted from the pixel. OLED pixels are emitters that emit light over a wide range of directions, and electrophoretic pixels are reflectors that reflect light over a wide range of directions. In the context of the present invention, such emitters and reflectors are also called diffuse emitters and diffuse reflectors, respectively. For a conventional (2D) display, OLED displays have a clear advantage over LCD displays that require a backlight and which, without taking special measures, emit light only in a narrow beam. However, the diffuse emission of the OLED material also poses a challenge as a lot of light is recycled inside the organic layers and is not emitted giving rise to a low efficiency. To improve, this various solutions have been sought to improve the out-coupling of the light out of the OLED.

However this improvement for 2D displays is in fact a problem for 3D autostereoscopic OLED displays. The solutions for increasing the light output cannot be used in autostereoscopic lenticular displays, as the light intended to be emitted from one lenticular lens may be reflected in the glass to a neighbouring lens. This reduces contrast and increases crosstalk.

Reflective displays such as electrophoretic and electrowetting displays may give rise to similar drawbacks as discussed above for emissive displays in the form of OLED displays.

Thus, there is a conflict between the desire for using emissive and reflective displays and the desire for low crosstalk within a 3D autostereoscopic display.

SUMMARY OF THE INVENTION

According to the invention, there is provided an autostereoscopic display device comprising:

a display arrangement comprising an array of spaced pixels;

a light guiding arrangement comprising an array of light guide columns, with one column over each display pixel or a group of pixels, wherein the light guide columns comprise a side wall which tapers outwardly to define a funnel shape with the pixel or pixels at the smaller base of the funnel; and an autostereoscopic lens arrangement comprising a plurality of lenses over the light guiding arrangement.

In an embodiment of the invention, the display arrangement is an emissive display, such as an electroluminescent display, for example an OLED display. In a further embodiment of the invention, the display arrangement is a reflective display, such as an electrophoretic display or an electrowetting display The function of the light guiding arrangement in the form of light funnels is to deliberately reduce the aperture ratio of the display pixel. The funnels have a construction specifically optimised for the autostereoscopic display, in particular the lens arrangement, to reduce crosstalk and improve performance.

A plurality of pixels can be provided beneath each lens of the lens arrangement (although a single microlens per pixel is also possible). For example, the autostereoscopic lens arrangement can comprise a plurality of lenticular lenses extending in a pixel column direction or inclined at an acute angle to the pixel column direction, wherein each lens covers a plurality of pixel columns. The lenses thus cover a number of columns of pixels. By reducing the amount of light extending parallel or at a small angle to the plane of the display, cross talk is reduced.

The side wall can have a first slope on one side in the width direction of the lenticular lens and a different second slope on the opposite side. This means that the way the funnel limits the angular spread of light is different at different sides of the pixel. The pixels are at different positions under the lens, and this feature enables the angle of incidence on the lens surface to be controlled in dependence on the local shape of the lens at the edges of the light cone emanating from the pixel. The base of the funnel can have a width which corresponds to the width of the emissive or reflective area of the pixel, which will be denoted the "pixel width".

Another way to change the angular spread of light on different sides is for the side wall to have the same slope on both sides in the width direction of the lenticular lens, but the base of the funnel can have a width which is greater than the pixel width, and is non-symmetrically positioned with respect to the pixel.

The funnel shapes can merge at their larger top, thereby filling the spacing between the pixels, or else the funnel shapes can be spaced at their top. In this way, the side wall slope can be larger or smaller, to control the amount of light collimation by the funnel.

The side wall can be reflective to define a light cone.

When the display arrangement is an electroluminescent display arrangement in a top-emitting implementation, the electroluminescent display arrangement comprises a substrate, an array of reflective anodes over the substrate, an array of electroluminescent layer portions over the anodes, and an array of transparent cathodes over the electroluminescent layer portions, wherein the light guiding arrangement and then the autostereoscopic lens arrangement are provided over cathodes.

Spacers can be provided between the pixels which project above the cathodes and over which the light guiding arrangement extends. A reflective coating can be provided over the spacers.

When the display arrangement is an electroluminescent display arrangement in a bottom-emitting implementation, the electroluminescent display arrangement comprises a substrate, the light guiding arrangement over the substrate, an array of transparent anodes over the light guiding arrangement, an array of electroluminescent layer portions over the anodes, and an array of reflective cathodes over the electroluminescent layer portions, wherein the autostereoscopic lens arrangement is provided on the opposite side of the substrate to the light guiding arrangement.

The invention also provides a method of displaying autostereoscopic images, comprising:

generating a pixellated image using a display arrangement comprising an array of spaced pixels;

guiding the pixel light output using a light guiding arrangement comprising an array of light guide columns, with one column over each display pixel or group of pixels, wherein the light guide columns comprise a side wall which tapers outwardly to define a funnel shape with the pixel or pixels at the smaller base of the funnel; and directing light from different pixels in different directions using an autostereoscopic lens arrangement comprising a plurality of lenses over the light guiding arrangement.

BRIEF DESCRIPTION OF THE DRAWINGS

An embodiment of the invention will now be described, purely by way of example, with reference to the accompanying drawings, in which.

DETAILED DESCRIPTION OF THE EMBODIMENTS

The invention provides an autostereoscopic display device comprising an a display arrangement comprising an array of spaced pixels. A light guiding arrangement has an array of light guide columns, with one column over each display pixel or over a group (such as a column) of pixels. The light guide columns comprise a side wall which tapers outwardly to define a funnel shape with the pixel at the smaller base of the funnel. The funnel provides collimation to reduce cross talk in the display, which is particularly problematic for 3D autostereoscopic displays.

Hereinbelow, embodiments of the present invention will be described on the basis of an electroluminescent display, which is an example of an emissive display. The skilled person will understand that the invention can be applied in lenticular lens based autostereoscopic display arrangements comprising any kind of emissive display, and also in lenticular lens based autostereoscopic display arrangements comprising any kind of reflective display, as in all these display types light will be directed (via emission or via reflection) from a pixel to the lenticular lenses over a wide range of directions.

The basic operation of a known 3D autostereoscopic display will first be described.

Figure 1:
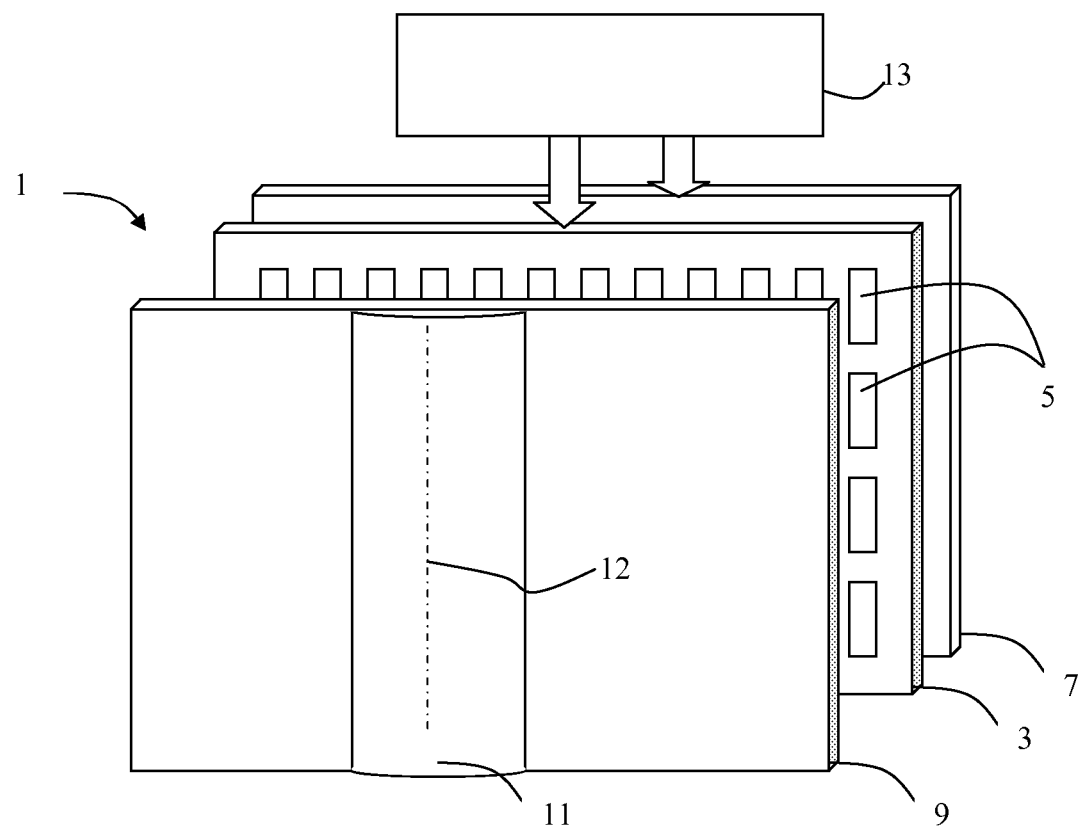
FIG. 1 is a schematic perspective view of a known autostereoscopic display device.

FIG. 1 is a schematic perspective view of a known direct view autostereoscopic display device 1 using an LCD panel to generate the images. The known device 1 comprises a liquid crystal display panel 3 of the active matrix type that acts as a spatial light modulator to produce the display.

The display panel 3 has an orthogonal array of display pixels 5 arranged in rows and columns. For the sake of clarity, only a small number of display pixels 5 are shown in the Figure. In practice, the display panel 3 might comprise about one thousand rows and several thousand columns of display pixels 5.

The structure of the liquid crystal display panel 3 as commonly used in autostereoscopic displays is entirely conventional. In particular, the panel 3 comprises a pair of spaced transparent glass substrates, between which an aligned twisted nematic or other liquid crystal material is provided. The substrates carry patterns of transparent indium tin oxide (ITO) electrodes on their facing surfaces. Polarising layers are also provided on the outer surfaces of the substrates.

Each display pixel 5 comprises opposing electrodes on the substrates, with the intervening liquid crystal material therebetween. The shape and layout of the display pixels 5 are determined by the shape and layout of the electrodes. The display pixels 5 are regularly spaced from one another by gaps.

Each display pixel 5 is associated with a switching element, such as a thin film transistor (TFT) or thin film diode (TFD). The display pixels are operated to produce the display by providing addressing signals to the switching elements, and suitable addressing schemes will be known to those skilled in the art.

The display panel 3 is illuminated by a light source 7 comprising, in this case, a planar backlight extending over the area of the display pixel array. Light from the light source 7 is directed through the display panel 3, with the individual display pixels 5 being driven to modulate the light and produce the display.

The display device 1 also comprises a lenticular sheet 9, arranged over the display side of the display panel 3, which performs a view forming function. The lenticular sheet 9 comprises a row of lenticular elements 11 extending parallel to one another, of which only one is shown with exaggerated dimensions for the sake of clarity.

The lenticular elements 11 are in the form of convex cylindrical lenses, and they act as a light output directing means to provide different images, or views, from the display panel 3 to the eyes of a user positioned in front of the display device 1.

The device has a controller 13 which controls the backlight and the display panel.

The autostereoscopic display device 1 shown in FIG. 1 is capable of providing several different perspective views in different directions. In particular, each lenticular element 11 overlies a small group of display pixels 5 in each row. The lenticular element 11 projects each display pixel 5 of a group in a different direction, so as to form the several different views. As the user's head moves from left to right, his/her eyes will receive different ones of the several views, in turn.

In the case of an LCD panel, a light polarising means must also be used in conjunction with the above described array, since the liquid crystal material is birefringent, with the refractive index switching only applying to light of a particular polarisation. The light polarising means may be provided as part of the display panel or the imaging arrangement of the device.

Figure 2:
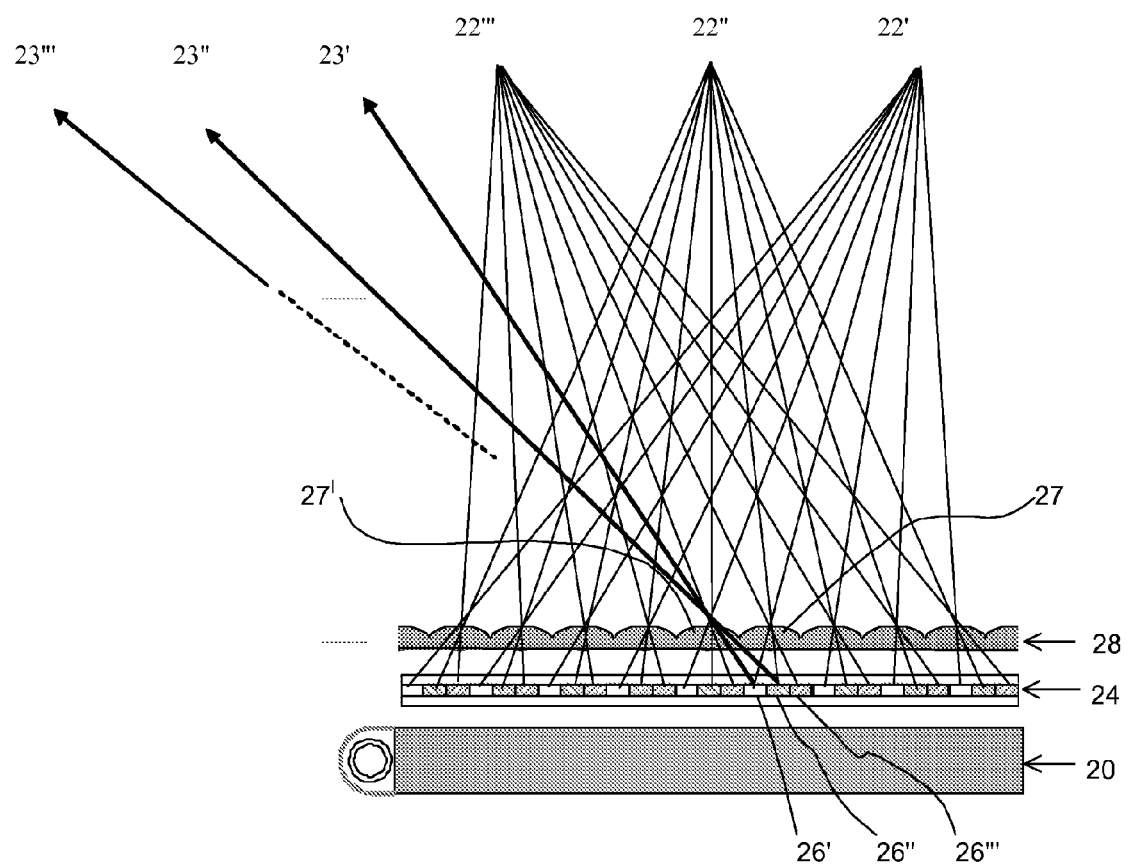
FIG. 2 shows how a lenticular array provides different views to different spatial locations.

FIG. 2 shows the principle of operation of a lenticular type imaging arrangement as described above and shows the backlight 20, display device 24 such as an LCD and the lenticular array 28. FIG. 2 shows how the lenticular arrangement 28 directs different pixel outputs to three different spatial locations 22', 22", 22'". These locations are all in a so-called viewing cone, in which all views are different. The views are repeated in other viewing cones, which are generated by pixel light passing through adjacent lenses. The spatial locations 23', 23", 23'" are in the next viewing cone.

The use of an OLED display avoids the need for a separate backlight and polarizers. OLED promises to be the display technology of the future. However, a problem currently with OLED display is the light extraction out of the device. Without taking any measures the light extraction out of the OLED can be as low as 20%.

Figure 3:
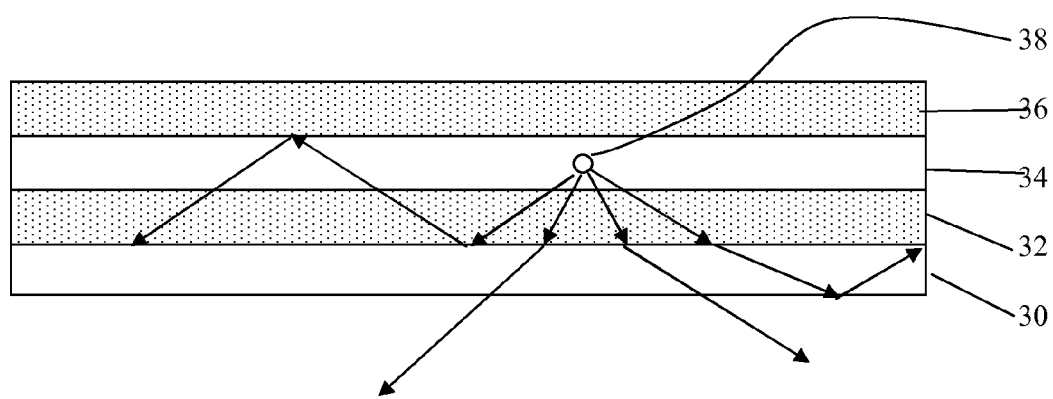
FIG. 3 schematically shows the structure of a single pixel of an OLED display, and in the form of a backward emitting structure.

FIG. 3 schematically shows the structure of a single pixel of an OLED display, and in the form of a backward emitting structure (i.e. through the substrate).

The display comprises a glass substrate 30, a transparent anode 32, a light emissive layer 34 and a mirrored cathode 36.

The lines represent the path light can take when emitted from a point 38 in the organic layer. As the light is emitted from the source it can travel in all directions. When the light reaches the transition from one layer to another layer the difference between the refractive index of each of the layers determines whether the light can escape one layer and get into the next. The refractive index is determined by the speed of light in the material and is given by Snell's law:

$$\frac{\sin\theta_1}{\sin\theta_2} = \frac{v_1}{v_2} = \frac{n_2}{n_1}$$

v=velocity (m/s)
n=refractive index (unitless)

In the example of FIG. 3 the refractive index of the organic material forming the light emissive layer 34 is high (n=1.8) while the refractive index of glass is 1.45.

When the angle of incidence of light that travels from a material with a high refractive index to a material with a low refractive index is large enough, the light cannot leave the material. The angle of incidence the critical angle and is given by α=arcsin($n_2/n_1$) for the organic material into glass. This gives 54 degrees.

Thus, it is clear that a lot of the light generated in the organic layer never leaves the layer but stays inside the material, where it is re-absorbed and drives another photon emission or turns into heat.

The same happens for the light that does leave the organic layer and enters the glass substrate. A lot of light cannot leave the glass at the glass to air interface.

Several solutions have been proposed both for ensuring the coupling of light out of the organic layers into the glass and for coupling the light out of the glass into the air.

The article by D. S. Mehta et. Al, "Light out-coupling strategies in organic light emitting devices" *Proc. of ASID* '06, 8-12 October, New Delhi gives an overview of the various solutions.

Whilst OLED devices are typically bottom emitting, and emit light through the glass substrate, another approach is to make the OLED stack top emitting such that the light emits through a transparent cathode and a thin encapsulating layer and not through the glass substrate. In general, different approaches to increasing the light extraction work better (or only) with either top or bottom emitting OLED structures.

The invention is described below based mainly on the use of a top-emitting OLED display. However the basic principle behind this invention can also be used with a bottom emitting OLED display, and all embodiments are applicable to both top and bottom emitting OLED structures.

Whilst the known solutions help to improve the light extraction efficiency up to 80% for lighting applications and for 2D displays, they do not provide a good solution for an autostereoscopic displays. A problem occurs when fitting a lenticular lens on the OLED display for creating an autostereoscopic TV. Even with a top emitting OLED, light will still be injected into a relatively thick glass layer causing the problems highlighted above, and a substantial amount of light will remain in waveguide mode in the glass. In principle, using a lenticular lens improves the light extraction from the glass into air as compared to a bottom emitting OLED but for a 3D display this has the side effect of reducing contrast and increasing crosstalk. This is a particular issue for 3D displays. For 2D displays, in many cases adjacent pixels will display the same colour (i.e. white or coloured areas of a screen, lines of single colour etc.) so that if any light escapes from a neighbouring pixel, this will simply add to the desired colour. However, in a 3D display, adjacent pixels do not in general have any relationship to each other, as they belong to different views and will generally be of different colour content. Thus, if any light escapes from a neighbouring pixel, this will seriously affect the quality of the image.

Furthermore, a substantial amount of light will still stay in waveguide mode in the glass. Part of this will be re-absorbed.

Figure 4:
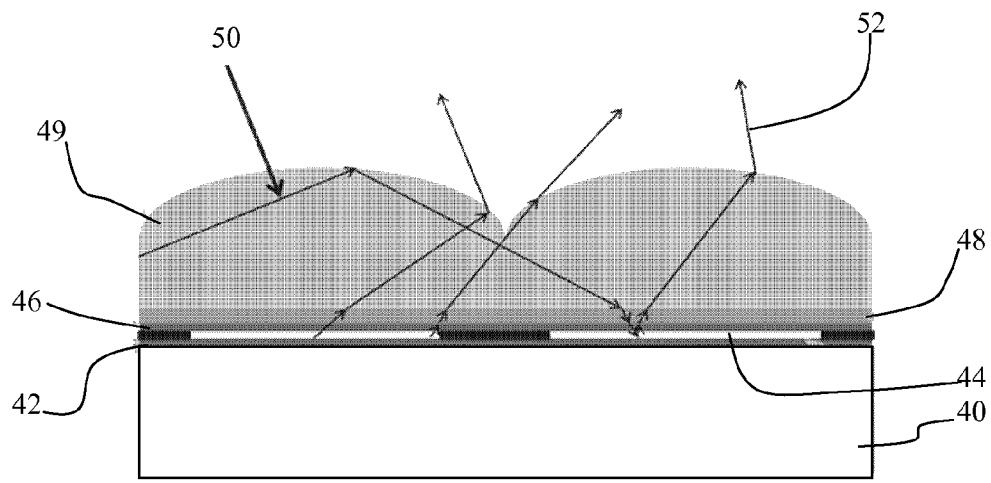
FIG. 4 shows how the light paths are affected when applying a lenticular lens to a top emitting structure.

FIG. 4 shows how the light paths are affected when applying a lenticular lens to a top emitting structure. The top emitting structure comprises a glass substrate 40, mirrored anode 42, light emissive layer defining pixels 44 and a transparent cathode 46. A sealing and passivation layer 48 is between the cathode 46 and the glass lenticular array 49.

As illustrated in FIG. 4, light is generated in the organic layer and some light enters the glass of the lenticular arrangement 49. Some of the light will stay in waveguide mode in the glass by virtue of the internal reflections 50 and enter the optical path of a neighbouring view (or pixel/subpixel). Here it may be reflected back and leave through the lens (as shown for light ray 52) or it may be re-absorbed in the pixel.

If the light does leave the lens of the neighbouring view it will create crosstalk.

The invention provides a pixel structure which deliberately reduces the aperture ratio of the OLED emitter and adds light redirecting structures (in the form of funnels/cones) designed to redirect light emitted above the critical angle into directions more perpendicular to the surface of the display, whereby more light will be emitted.

Figure 5:
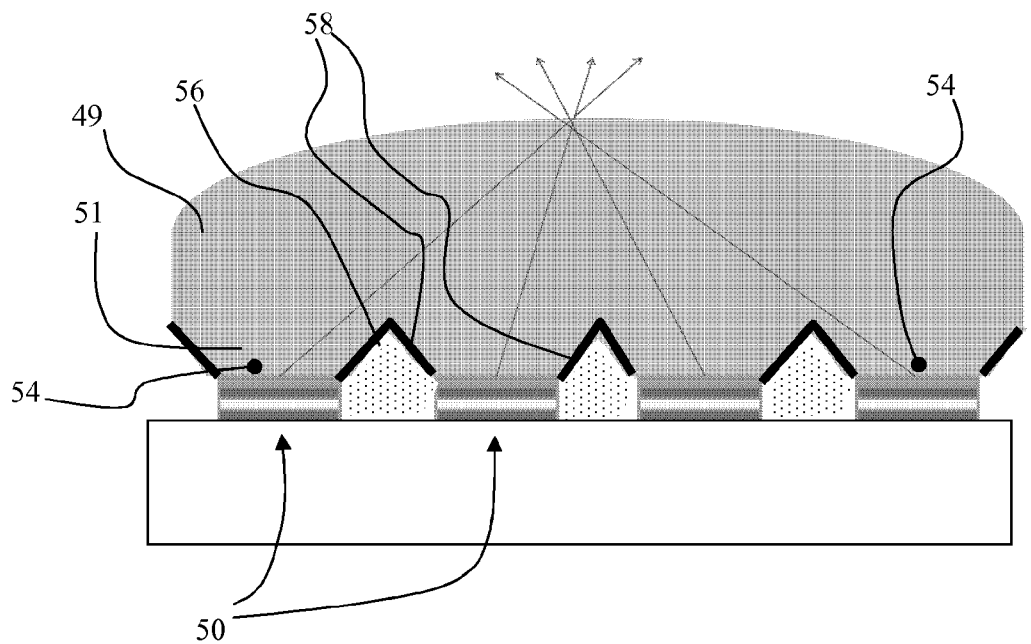
FIG. 5 shows a first example of pixel structure in accordance with the invention.

FIG. 5 shows a first example of pixel structure in accordance with the invention.

Several pixels 50 are formed under a single lenticular lens 52, so that the lens optics results in the light from different pixels being directed in different directions. FIG. 5 shows a top emitting 3D OLED display.

The structure is provided with light out-coupling structures 51. These structures 51 extend over the pixels. They have a base 54 which overlies the pixel, and they widen (diverge) as they increase in height above the pixel. This defines a funnel type structure, with the pixels at the smaller end of the funnel. The funnel functions as a light collimator. Supports 56 are defined between the bases 54 and these are present as part of the method of manufacture. The supports 56 taper, so that inclined side faces are defined. The supports are coated with a reflective surface so that the side faces are reflective. These reflective surfaces limit the progression of light in a direction parallel or near parallel to the substrate between the pixels, and thereby they limit the waveguide problem.

The refractive index of the light out-coupling structures is chosen with respect to the adjacent layers to avoid waveguiding within the material of the structures 51.

For example, the light out-coupling structures 51 can consist of a material with refractive index n greater than that of air and less than that of the material of the adjacent layer of the OLED stack (i.e. $1<n<1.8$), so that they have a refractive index between that of the OLED stack material and air. This will be termed an "intermediate refractive index".

A higher refractive index would cause issues of extracting light at the final interface, hence the upper limit for the refractive index of the structures 51. n=1 is the physical lower limit. However, refractive index of the structures 51 may be higher than that of the lenticular lens material, as this will enhance extraction of the light from the OLED.

The lenticular lens structure 49 is provided over the light out-coupling structures 51.

The shape of the structures 51 can be obtained by structuring of photoresist or asymmetric etching of a layer in order to form the supports 56 with their slanted sides, followed by the deposition of a reflective coating 58, such as a thin film of aluminum. The supports 56 and the structures 51 can be of the same material, such as photoresist.

In this case, the structures 51 are built up on top of the OLED after it is deposited. The structures 51 may have the form of a rounded flowerpot with slanted sides in all directions—FIG. 5 shows a cross section in a direction perpendicular to the direction of the lenticular lens.

It is also possible to create structures with a more square, rectangular, triangular, hexagonal (or other shaped) top profile, and it is not necessary that all sides are slanted and/or reflective.

The structure 51 operates by redirecting the lambertian emitted light of the OLED in the medium of intermediate refractive index, such that the light is incident on the glass/air interface (at the lens output) at lower angles than usual. Ideally, light is restricted to an angle below that of the critical angle (typically 42°) for glass with n=1.5. In this manner, more or all light is extracted, and the crosstalk reduced.

To create space between the pixels for the supports 56, the pixel spacing is increased, and thereby the area of the emitter areas is reduced. However, the increased optical efficiency at least partially compensates for the emitter surface reduction.

Figure 6:
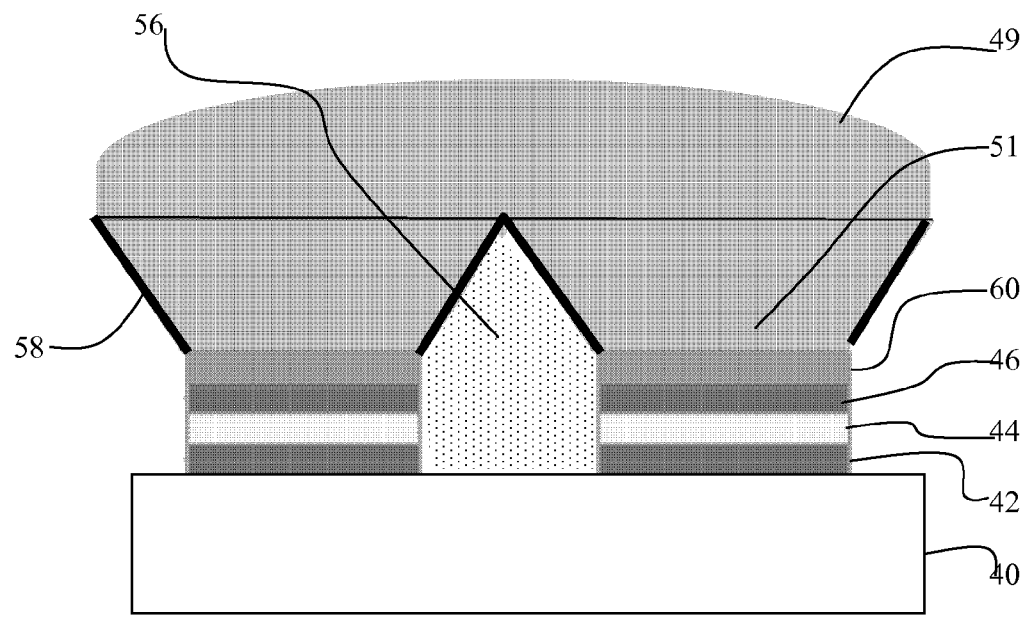
FIG. 6 shows the pixel structure of FIG. 5 in more detail.

FIG. 6 shows the structure in more detail. The anode 42, emitter material 44 and cathode 46 are the same as in FIG. 4, hence the same reference numbers are used. A thin cover film 60 is provided over the OLED structure and this can include a getter layer.

Figure 7:
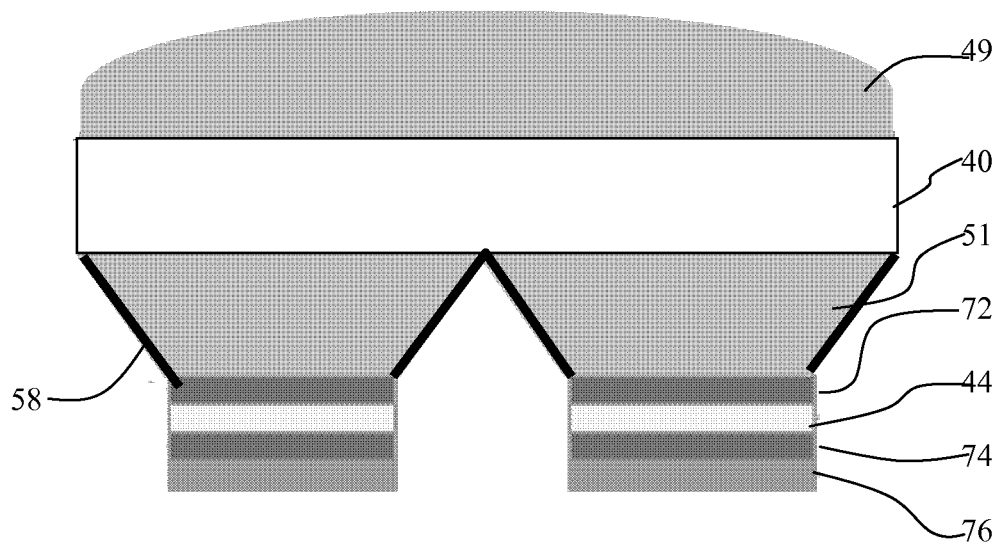
FIG. 7 shows a second example of pixel structure in accordance with the invention.

FIG. 7 shows the same concept applied to a bottom emitting OLED.

The OLED structure comprises the glass substrate 40, the light out-coupling structure 51 and its reflective coating 58, a transparent anode 72, the light emitting layer 44 and a mirrored cathode 74. A thin film cover layer 76 and getter material covers the cathode 74.

In this design, light is emitted through the glass substrate 40 before passing through the lenticular lens 49. Again, the light out-coupling structure 51 consist of a material with refractive index n greater than that of air and typically less than that of the OLED material. Structuring of the material of the layer 51 (such as photoresist (SU8)) is carried out to form the slanted sides, followed by the deposition of a reflective coating, such as a thin film of aluminum. In this case, the structures 51 are built up on the glass substrate before the OLED stack is deposited. The structures may again have the form of a rounded flowerpot with slanted sides in all directions or other shapes.

The structure 51 operates in the same way as described above, redirecting the lambertian emitted light of the OLED in the medium of intermediate refractive index, such that the light is incident on the glass/air interface at lower angles than usual.

One of the issues with applying the design shown in FIGS. 6 and 7 is that the lens function means that the light from the pixel is imaged onto different parts of the lens, which are not directly above the emitter pixel area, and this means that light rays with angles above the critical angle may result.

Different solutions to this problem are described below.

Figure 8:
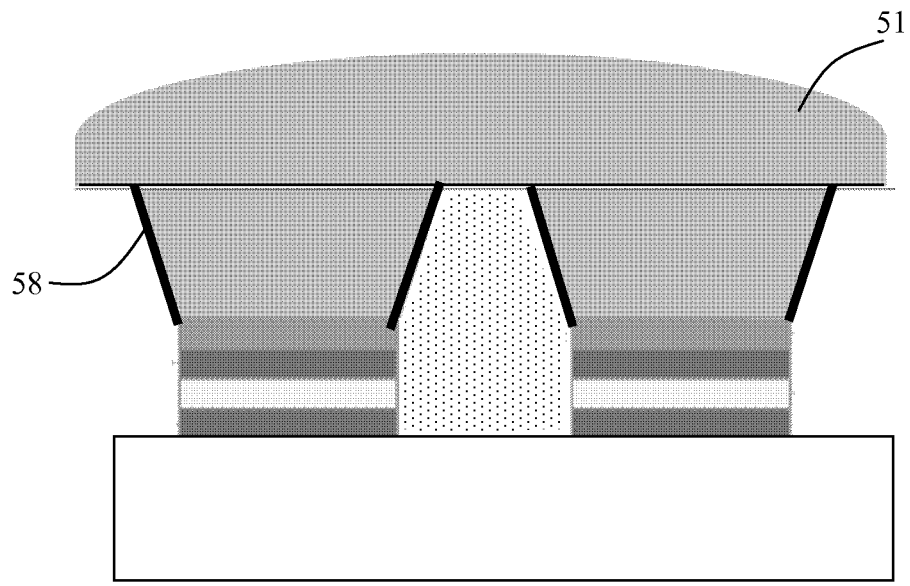
FIG. 8 shows a third example of pixel structure in accordance with the invention.

In the example of FIG. 8 (which may be applied to both top and bottom emitting OLED structures) the reflecting surfaces 58 are arranged such that the light is emitted in a more collimated manner.

This is achieved by having steeper side surfaces. Alternatively, more collimated light can be obtained by increasing the height of the side surfaces.

This means that the range of angles at which light can exit the funnel without reflection is reduced. Light which is almost parallel to the substrate and is reflected by the side walls will still have a shallow angle when it leaves the funnel. However, the longer the funnel, the better the collimation (since at each reflection, the light approaches the normal). A longer funnel and steeper sides will however reduce the light efficiency since more light will be reflected. Thus, there is a compromise between light efficiency and degree of collimation when selecting the length of the funnel and the steepness of the sides.

The degree of collimation should be increased sufficiently to account for the steepest angle of slope of the lenticular lens—which may be up to 20°, adjusted to account for the intermediate refractive index of the medium.

For example, light emission may be limited to around 30-35° in typical cases. This is achieved by arranging the reflective surfaces at the steeper angle as shown in FIG. 8. In this manner, there will be less light incident on the (local) surface of the lens at angles beyond the critical angle, so that light is emitted more efficiently and cross talk is reduced. However, one issue of this approach is that some higher angle repeated views may be suppressed by the over-collimation of the light.

In the design of FIG. 8, the bottom of the light out-coupling structures as well as the top are spaced apart, and the steeper sides create a light tube.

The angles of the side walls will depend on the width of the lens and the overall viewing angle of the display. In particular, the side walls will define the maximum angle at which light is directly emitted, and this maximum angle is reduced by the steeper side walls in FIG. 8. In the examples of FIGS. 6 and 7, the side walls may typically be in the range 30 to 60° to the normal (normal to the substrate area) whereas in the example FIG. 8, the side walls may typically be in the range 10 to 40° to the normal.

The angle of the walls determines how the light is collimated. If the walls are too steep, rays from the emitter will hit both tapered walls before going out. This means that the apparent origin of the ray may become another pixel, which is to be avoided as this effectively corresponds to crosstalk.

The angles should essentially be chosen to avoid wave-guiding, and this will depend on the lens shape and dimensions.

Figure 9:
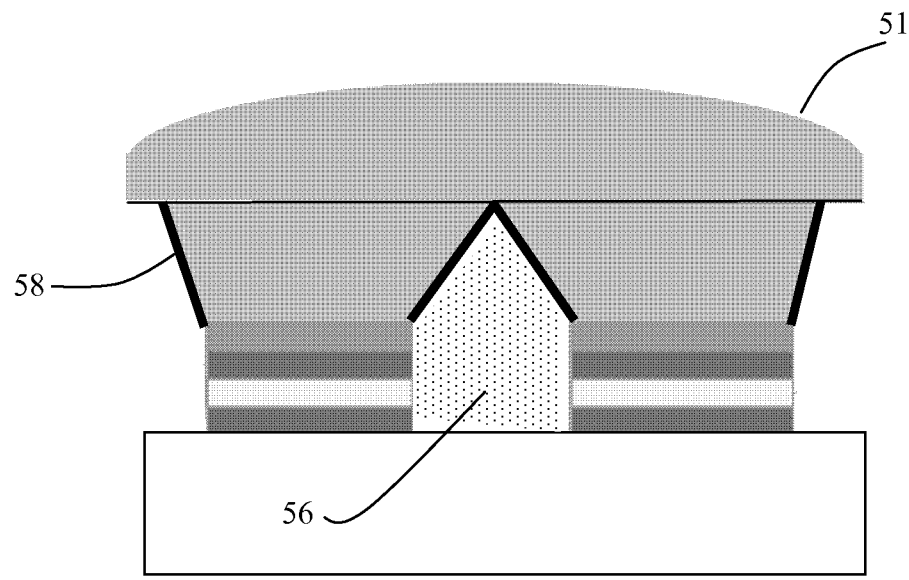
FIG. 9 shows a fourth example of pixel structure in accordance with the invention.

In the example of FIG. 9 (which again may be applied to both top and bottom emitting OLED structures) the reflecting surfaces 58 are arranged such that the light is emitted in an asymmetric collimated manner. This is achieved by giving the light out-coupling structures different slant angles on different sides, where a "side" is taken to be in the direction of the lens width. Typically, the asymmetry of collimation should be such as to achieve an equal degree of collimation on both sides of the light emission profile from the pixel as imaged by the lens.

Collimation should be at around the critical angle on both sides of this light emission cone. In this manner, there will be less light incident on the (local) surface of the lens at angles beyond the critical angle, whereby light is emitted more efficiently and cross talk is reduced and there is a reduced suppression of higher angle repeated views.

Figure 10:
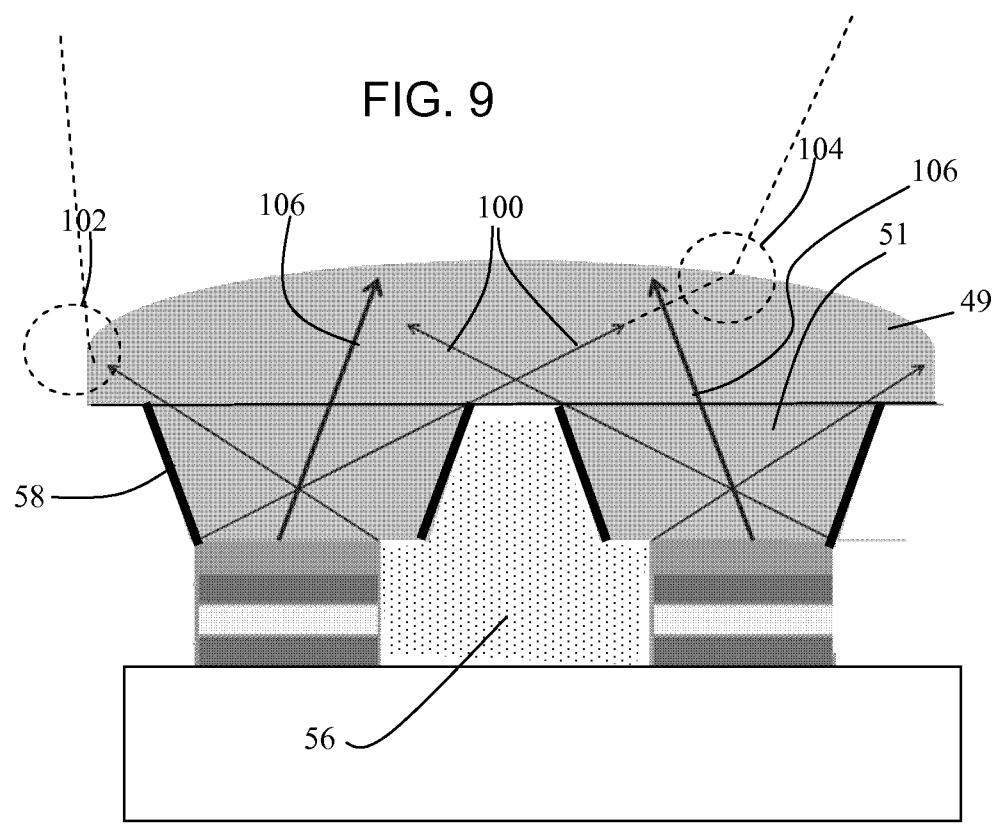
FIG. 10 shows a fifth example of pixel structure in accordance with the invention.

FIG. 10 shows a further modification (which again may be applied to both top and bottom emitting OLED structures) with asymmetric pixel emitter placement with respect to the light out-coupling structure.

The reflecting surfaces 58 are arranged such that the light is emitted in an asymmetric collimated manner. This is achieved by further reducing the aperture of the emitters compared to the base 54 and positioning the OLED emitters in an asymmetric manner compared to the light out-coupling structures. In this way, light is emitted in an asymmetric cone despite the fact that the angle of slope of the reflective surfaces is the same on both sides of the pixel.

FIG. 10 shows more clearly how the light out-coupling structure provides collimation. The rays shown as 100 are the steepest rays that can directly escape from the light out-coupling structure. In this case and for simplicity, the light out-coupling structures 51 are assumed to have the same refractive index as the glass of the lenticular 49 so that no angle change is shown.

As in the example of FIG. 9, the asymmetry of collimation should be such as to achieve an equal degree of collimation on both sides of the direction of light emission of the pixel as imaged by the lens. The angle the light beam makes with the normal to the lens surface at locations 102 and 104 is the same, and the light cone leaving the lens surface is symmetric about the desired emission direction of the viewing cone, shown as 106. Thus, internal reflection is avoided, and at the same time the desired output light distribution is maintained.

Note that the figures are schematic, and the light rays should not be considered as showing the correct relative angles.

The structures 51 influence the light cone at the (local) emission surface of the lenticular lens. The ideal spread (the light envelope defined by the light leaving locations 102 and 104) will be with the most extreme light rays at exactly the critical angle for total internal reflection (TIR). However, steeper side walls will result in these extreme rays having an angle less than the TIR angle (i.e. 80% of TIR).

In both cases, the angle made by the steepest rays which can directly escape from the light funnel is around or below the critical angle, so that there will be less light incident on the (local) surface of the lens at angles beyond the critical angle, such that light is emitted more efficiently and cross talk is reduced.

The advantage of this example as compared to the example of FIG. 9 is that it is only necessary to define a single angle of slope of the reflective surfaces for the entire display. This is a major technological advantage, as the creation of the slope can be carried out in a single processing step (e.g. an etching step). In addition, it is possible to fine tune displays to different optical (lenticular) structures or desired viewing cones simply by adjusting the layout of the position and size of the emitter in the pixel. This is simply a choice of mask design whilst maintaining the same manufacturing process.

The thick arrows 106 indicate the central direction of the emission cones, the thin arrows 100 indicate the edges of the emission cones (drawing not to scale).

In an auto-stereoscopic 3D display, the presence of the lenticular (or other) lens array means that the required direction of light from the pixel to the lens will be spatially varying, depending upon where the pixel is situated compared to the lens, and the direction of the light cone that will form the view. Some examples above enable the out-coupling optics to be adapted from pixel to pixel, in a manner following the local geometry as defined by the 3D generating optics.

The example described above has light funnels above each pixel. To form this, the support 56 surround the pixel and defines a side wall all around the pixel. A grid is defined by the support 56 with opening at the pixels.

Figure 11:
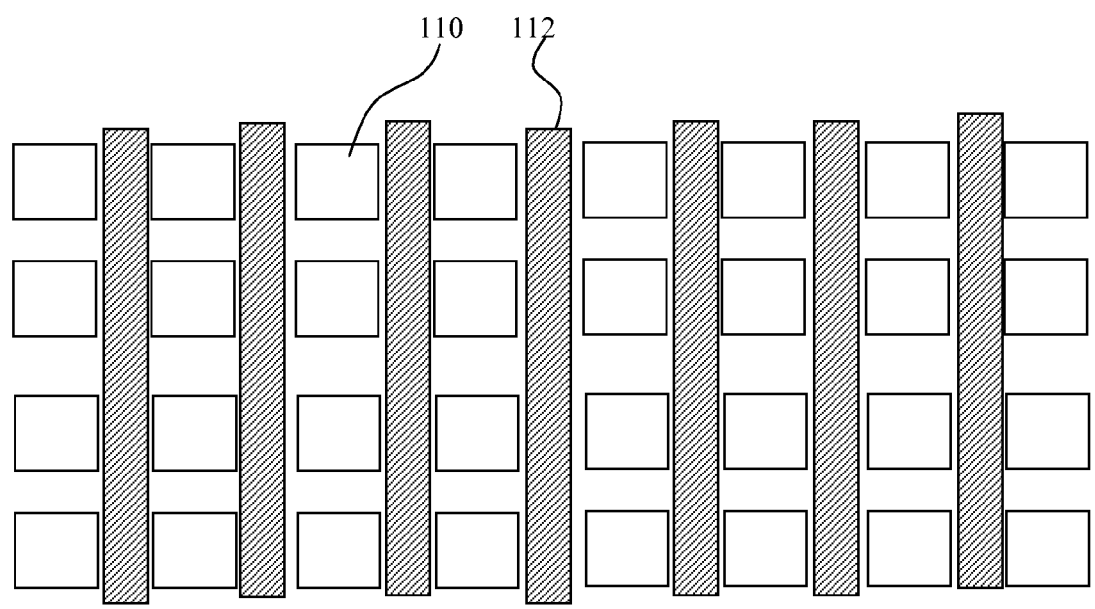
FIG. 11 shows one example of implementation of the invention in plan view.

However, the light out-coupling structures are only essential in the row direction of the pixel, across the lenticular lens width, since it is cross talk between views across the row direction that is a problem. Thus, the funnel sides may be only in the spaces between pixels in the row direction. FIG. 11 shows a schematic plan view of the pixels 110 and spacers 112 which are only between the columns so that the light funnel shape is only in the lens width direction. In this case, each funnel is a long rectangle, and covers a column of pixels.

Instead, the spacers may surround each pixel thereby defining a cone around and above each pixel. The bottom emitting examples do not use spacers to define the funnel side walls, but the same issues apply in that the light collimation can optionally be limited to the lens width direction.

The OLED typically comprises an active matrix display, with an array of row and column conductors, with the pixels defined at the intersection, and with a respective switching element, and optionally current driving electronic circuitry associated with each pixel.

The solution of the invention is somewhat counterintuitive, as usually great effort is taken to maximise the aperture of the display, and to ensure that the structure of the display is uniform across the display (i.e. is not adapted to the 3D optics).

The invention enables the pixel optics to be adjusted according to the geometry of the 3D optics of the display at the position of the pixel to increase the light extraction from the OLED via the lenticular into the air to improve performance. Furthermore, because of the form of the lenticular lens (i.e. top and bottom surfaces are tilted to each other), it is necessary that in some cases the optical structures are defined to reduce the light directions to be significantly below the critical angle of the light into the lenticular lens structure, in order that the light is emitted at the top of the lenticular lens.

The examples of the invention described above are applicable to any OLED based display where the direction perpendicular to the surface of the display varies across the display, such as might be realised in multi-focus displays, displays with touch pads added on top of the display, displays with tactile structures added to the surface etc.

The transparent material used for the cathode or anode can typically comprise ITO.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. An autostereoscopic display device comprising:
a display arrangement comprising an array of spaced pixels;
a light guiding arrangement comprising an array of light guide columns, with one light guide column over each display pixel or a group of pixels, wherein the light guide columns comprise a side wall which tapers outwardly to define a funnel shape with the pixel or pixels at the smaller base of the funnel; and
an autostereoscopic lens arrangement comprising a plurality of lenticular lenses over the light guiding arrangement, the lenticular lenses extending in a pixel column direction or inclined at an acute angle to the pixel column direction, wherein each lens covers a plurality of pixel column widths,
wherein light guide columns limit the angular spread of light differently at different sides of the underlying pixel, because either:
the side wall has a first slope on one side in the width direction of the lenticular lens and a different second slope on the opposite side; or
the side wall has the same slope on both sides in the width direction of the lenticular lens, and the base of the funnel has a width which is greater than the pixel width, and is non-symmetrically positioned with respect to the pixel.

2. The device as claimed in claim 1, wherein the display arrangement is an emissive display arrangement.

3. The device as claimed in claim 2, wherein the emissive display arrangement is an electroluminescent display arrangement.

4. The device as claimed in claim 1, wherein the display arrangement is a reflective display arrangement.

5. The device as claimed in claim 1, wherein a plurality of pixels is provided beneath each lens of the lens arrangement.

6. The device as claimed in claim 1, wherein the side wall has a first slope on one side in the width direction of the lenticular lens and a different second slope on the opposite side and the base of the funnel has a width which corresponds to the pixel width.

7. The device as claimed in claim 1, wherein the funnel shapes merge at their larger top, thereby filling the spacing between the pixels.

8. The device as claimed in claim 1, wherein the funnel shapes are spaced at their top.

9. The device as claimed in claim 1, wherein the display arrangement is an electroluminescent display arrangement that comprises a substrate, an array of reflective anodes over the substrate, an array of electroluminescent layer portions over the anodes, and an array of transparent cathodes over the electroluminescent layer portions, wherein the light guiding arrangement and then the autostereoscopic lens arrangement are provided over cathodes.

10. The device as claimed in claim 9, further comprising spacers between the pixels which project above the cathodes and over which the light guiding arrangement extends.

11. The device as claimed in claim 10, further comprising a reflective coating over the spacers.

12. The device as claimed in claim 1, wherein the display arrangement is an electroluminescent display arrangement that comprises a substrate, the light guiding arrangement over the substrate, an array of transparent anodes over the light guiding arrangement, an array of electroluminescent layer portions over the anodes, and an array of reflective cathodes over the electroluminescent layer portions, wherein the autostereoscopic lens arrangement is provided on the opposite side of the substrate to the light guiding arrangement.

13. An autostereoscopic display device comprising:
a display arrangement comprising an array of pixels;
a light guiding arrangement comprising an array of light guide columns, with one light guide column over a plurality of pixels, wherein the light guide columns comprise a side wall which tapers outwardly to define a funnel shape with the plurality of pixels at the smaller base of the funnel; and
an autostereoscopic lens arrangement comprising a plurality of lenticular lenses over the light guiding arrangement, wherein each lens covers a plurality of pixel column widths,
wherein light guide columns limit the angular spread of light differently at different sides of the underlying pixel, by the side wall having a first slope on one side in the width direction of the lenticular lens and a second slope on the opposite side and the base of the funnel has a width which is greater than the pixel width, and is non-symmetrically positioned with respect to the pixel.

14. The autostereoscopic display device of claim 13, wherein the first slope and the second slope are either equal or different.

15. The autostereoscopic display device of claim 13, wherein the lenticular lenses extend in a pixel column direction or inclined at an acute angle to the pixel column direction.

\* \* \* \* \*